United States Patent

Foster

[11] Patent Number: 6,114,171
[45] Date of Patent: *Sep. 5, 2000

[54] ADDITIVE MANAGEMENT SYSTEM

[75] Inventor: James Joseph Foster, Clifton Forge, Va.

[73] Assignee: Westvaco Corporation, New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/954,038

[22] Filed: Oct. 20, 1997

[51] Int. Cl.[7] .................................................. G01N 35/00
[52] U.S. Cl. .............................. 436/55; 162/198; 702/23; 702/30
[58] Field of Search .......................... 436/55; 364/468.01, 364/468.15, 468.16, 497, 499, 500; 162/198; 702/23, 30

[56] References Cited

U.S. PATENT DOCUMENTS

| | | |
|---|---|---|
| 3,617,717 | 11/1971 | Smith . |
| 3,962,029 | 6/1976 | Wettermark et al. . |
| 3,980,517 | 9/1976 | MacTaggart . |
| 4,042,328 | 8/1977 | Seymour . |
| 4,192,708 | 3/1980 | Bergstrom et al. . |
| 4,294,656 | 10/1981 | Beck et al. . |
| 4,402,604 | 9/1983 | Nash . |
| 4,758,308 | 7/1988 | Carr . |
| 4,952,280 | 8/1990 | Hemel et al. . |
| 5,104,485 | 4/1992 | Weyer . |
| 5,325,605 | 7/1994 | Carew . |
| 5,330,621 | 7/1994 | Visuri et al. . |
| 5,441,873 | 8/1995 | Knight et al. . |
| 5,532,928 | 7/1996 | Stanczyk et al. . |
| 5,542,542 | 8/1996 | Hoffmann et al. . |
| 5,712,990 | 1/1998 | Henderson . |
| 5,724,255 | 3/1998 | Smith et al. . |
| 5,800,181 | 9/1998 | Heinlein et al. . |

OTHER PUBLICATIONS

Chemical Abstracts CA104:94612. Sarma, K.R.K., Ber. Int. Kolloq. Verhuetung Arbeitsunfaellen Berufskrankh. Chem. Ind. (1985), vol. 10, pp. 143–156.

Tatum, Natl. SAMPE Symp. Exhib., [Proc.] (1985), 30(Adv. Technol. Mater. Processes), 1534–40.

*Primary Examiner*—Jan Ludlow
*Attorney, Agent, or Firm*—J. R. McDaniel; R. L. Schmalz

[57] ABSTRACT

This invention relates to chemical additive management systems. Such structures of this type, generally, allow a manufacturer to determine if a chemical additive to be used will contain a chemical component or reaction product that is of toxicological concern to the end-user.

3 Claims, 1 Drawing Sheet

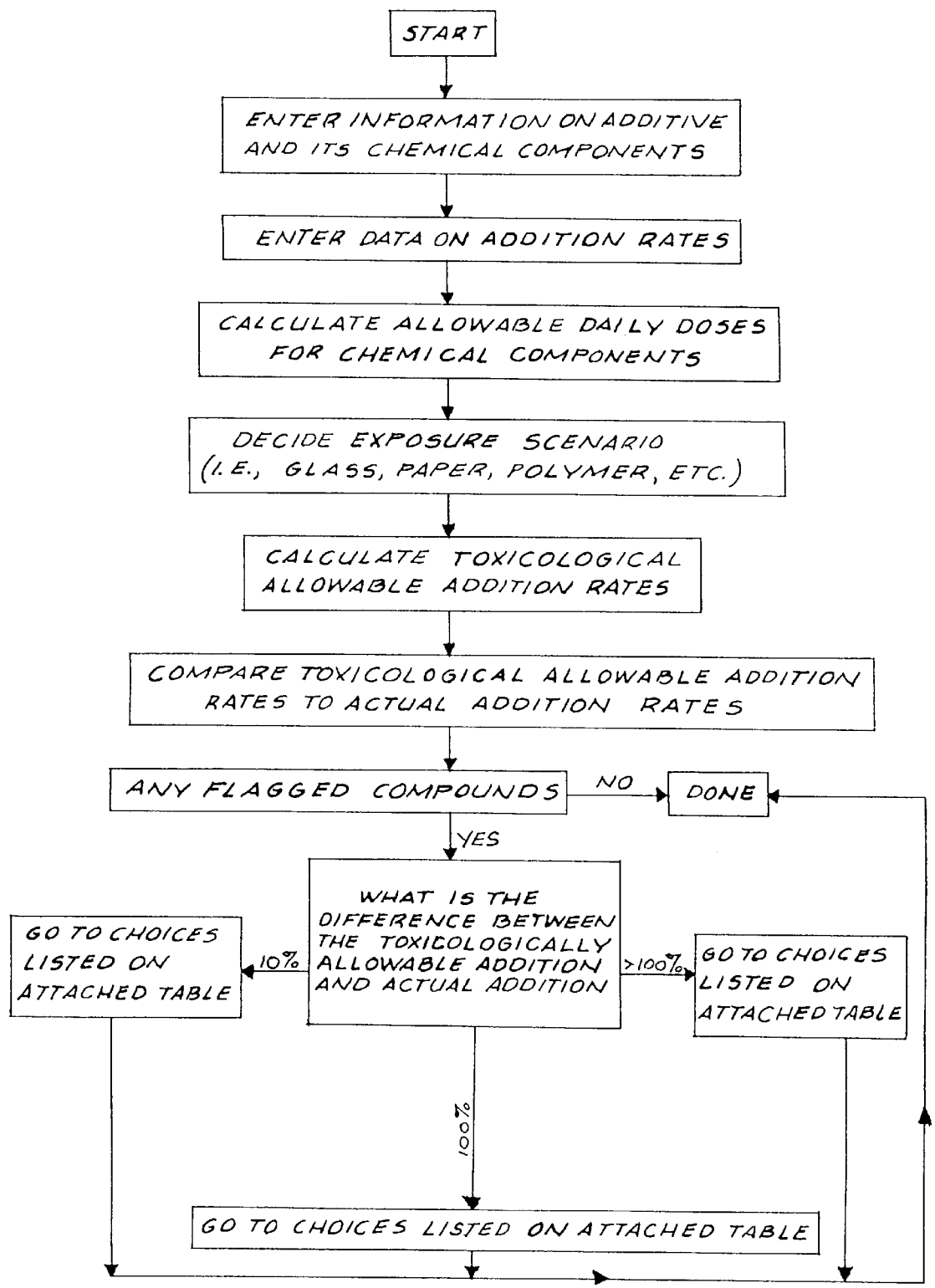
FIGURE

ADDITIVE MANAGEMENT SYSTEM

BACKGROUND OF THE INVENTION

1. Field of the Invention

This invention relates to chemical additive management systems. Such structures of this type, generally, allow a manufacturer to determine if a chemical additive to be used will contain a chemical component or reaction product that is of toxicological concern to the end-user, and if it does contain such a component, what action to take.

2. Description of the Related Art

Product safety is of critical importance to manufacturers. While all products entail some degree of risk, a manufacturer is strives to minimize the risk associated with their product. For example, the shroud on the bench saw that automatically covers the blade when the user is not sawing. This is an example of a physical device to make the product safe. One can also describe numerous examples of electrical devices that make a device safer such as double insulation or the use of ground fault interrupters.

As for minimizing the risk associated with chemicals and their use, one has to protect against immediate hazards (i.e., chemical burns, etc.) and/or long term hazards such as exposure to toxic compounds, etc. Minimizing the risks associated with an immediate hazard can be relatively straightforward. For example, one can use the lowest concentration of the hazardous chemical required to perform the intended function such as using the minimum amount of caustic in an oven cleaner.

However, it is more difficult to minimize the risks associated with long term exposure to chemical hazards. In this instance, one has to have knowledge of the chemical of concern, its concentration in the product, the toxicity of the chemical, do calculations to model the exposure a customer receives from use of the product and finally act upon this knowledge. While this can be done for products containing simple component mixes, complex component mixes can quickly become unwieldy.

Because of this difficulty, many companies have been reluctant to do a comprehensive study to investigate all the chemicals from a customer safety perspective. Instead, they focus on a few chemicals of particular toxicological interest and do not vigorously pursue the other chemicals. Thus, it is readily apparent there exists a need to develop a system whereby one can readily identify if an additive possesses a chemical component or reaction product that may pose a toxicological risk.

It is also known in U.S. Pat. No. 5,330,621 ('621) to P. Visuri et. al, entitled "Continuous Elemental Analysis of Process Flows", to employ a system which describes the chemical method for performing continuous elemental analysis on various process streams. While not designated for this purpose, the system may be modified to perform elemental analysis on heavy metals, which is a small subset of the chemicals of toxicological concern. Typically, the number of heavy metals of concern is approximately 17 while the number of chemicals of toxicological concern is greater than 500.

While the program embodied in the '621 reference can analyze for heavy metals, it does not inform the user if the heavy metal concentration is of concern, from which products the metals are originating and what to do with these elemental metals. Consequently, a more advantageous system, then, would be presented if the system could avoid and/or minimize expensive chemical testing of samples and still be able to perform the desired analysis.

It is apparent from the above that there exists a need in the art for an additive management system that will allow the user to determine when a chemical additive to be used will contain a chemical component or reaction product that is of toxicological concern, but which at the same time avoids and/or minimizes expensive chemical testing of samples while still being able to perform the desired analysis.

It is a purpose of this invention to fulfill this and other needs in the art in a manner more apparent to the skilled artisan once given the following disclosure.

SUMMARY OF THE INVENTION

Generally speaking, this invention fulfills these needs by providing a method for determining if a chemical additive to be used in a product produced by a manufacturing process will contain a chemical component or reaction product that is of toxicological concern as a result of the addition of the chemical additive to the manufacturing process, comprising the steps of: cataloging a plurality of chemical additives to be added to a manufacturing process and amounts of the chemical additives which are originally desired to be added; determining the actual concentration of the chemical components and reaction products in the chemical additives; calculating a toxicologically allowable concentration of the chemical components and the reaction products in products produced by the manufacturing process; comparing the toxicologically allowable concentration with the actual concentration; identifying, if any, chemical components and reaction products and their actual concentrations which are greater than the toxicologically allowable concentration; and adjusting, if necessary, the manufacturing process to reduce the actual concentration such that the actual concentration is no greater than the allowable concentration, the improvement wherein for differences between the allowable and the actual concentration which are less than 10% of the allowable concentration, the method further comprises the step of: contacting any supplier of the chemical additive which was added to the manufacturing process which produced the chemical components or reaction products that have an actual concentration greater than the toxicologically allowable concentration, recalculating the actual concentration of the chemical components or reaction products that have an actual concentration greater than the allowable concentration and employing a qualified toxicological analyst to review the actual concentration, the allowable concentration, and the comparison between the actual and allowable concentrations, to determine if such a difference between the actual and allowable concentrations warrants a toxicological concern.

In certain preferred embodiments, if the difference between the actual and toxicologically allowable concentrations is between 10% and 100% of the toxicologically allowable concentration, the method is further comprised of the step of determining if the chemical components or reaction products are eliminated during the manufacturing process. Also, if the difference between the actual and allowable concentrations is greater than 100% of the allowable concentration, the method is further comprised of the step of performing a migration analysis of the chemical components or reaction products.

In another further preferred embodiment, chemical additives that will be used which may contain a chemical component or reaction product that is of toxicological concern to the end-user may be identified by the manufacturer such that the method avoids and/or minimizes the expensive chemical testing of samples.

The preferred additive management system, according to this invention, offers the following advantages: good stability; good durability; excellent economy through reduced chemical testing; excellent additive management; and excellent toxicological identification. In fact, in many of the preferred embodiments, these factors of economy, additive management and toxicological identification are optimized to the extent that is considerably higher than heretofore achieved in prior, known process management systems.

BRIEF DESCRIPTION OF THE DRAWING

The above and other features of the present invention, which will become more apparent as the description proceeds, are best understood by considering the following detailed description in conjunction with the accompanying FIGURE, in which:

FIGURE is a schematic illustration of a flow chart illustrating the additive management system, according to the present invention.

DETAILED DESCRIPTION OF THE INVENTION

With reference first to the FIGURE, there is illustrated an advantageous environment for use of the concepts of the invention. In this discussion, the following terms will be used:

| | |
|---|---|
| Product: | The item which is being manufactured (e.g., lemonade) |
| Additive: | A chemical or mixture of chemicals that are the ingredients in a product (e.g., powdered lemonade mix and water) |
| Chemical Component: | Distinct chemicals that make up an additive (e.g., sugar and lemon flavor in the powdered lemonade mix) |

It is to be understood that chemical components include both those chemicals directly added to the additive and contaminants that are not purposely added but are residual of the manufacturing process, naturally occurring in the additive, etc.

The above definitions should not be interpreted as a limiting factor in this disclosure. Rather, they are included simply to allow one skilled in the art to more clearly understand the present invention. To further assist those skilled in the art, the FIGURE shows the flow diagram for the present invention.

As the first step of the present invention, appropriate information is gathered on the chemical additive. This information can be conventionally placed in the memory of any suitable computer. This information can be, typically, obtained from Material Safety Data Sheets (MSDS), supplier technical bulletins, direct requests to the manufacturer for information, etc. The information needed includes, but is not limited to, standard names of the chemical components and the concentration of the chemicals in the additive. If the concentration of the chemical in the additive is unknown, the quantity can be estimated or determined by appropriate analysis.

Information is also needed on the amount of chemical additive to be used in the product being manufactured. Information on the intended use of the material, where it is added in the production process, citation of regulatory compliance, appropriate regulatory limits and other information that the user of the invention may deem useful, while not required may be included in the database.

The applicable toxicity values also need to be included. This information can be obtained from numerous sources, e.g., California Environmental Protection Agency's *Safe Drinking Water and Toxic Enforcement Act of* 1986 (*Proposition* 65), National Institute for Occupational Safety and Health's *Registry of Toxic Effects of Chemical Substances*, MSDS sheets, etc. Unfortunately, toxicity information can be expressed by several different methods and these need to be converted to the appropriate uniform unit. For this example, the toxicity values are converted to an Allowable Daily Dose (ADD).

ADDs represent an estimation of the dose resulting in a one-in-a-million risk (or other level of risk deemed appropriate by the user) of toxicological effect. Because long term toxicity is considered to be more reliable for evaluating chronic risk than short term data, long term data is typically used, when available, to calculate ADDs. ADDs are in units of milligrams of chemical per kilogram of body weight per day (mg/kg/day). ADDs express the value which can be ingested, inhaled, etc. without toxicological effects at a defined level of risk.

As mentioned above, toxicity values are expressed by a number of different methods, each of which require different techniques to convert it to an ADD. The following are several examples of the calculation and are not intended to be an exhaustive exhibition of all techniques, but rather they are simply illustrative of the conversion process.

For carcinogens, the allowable daily dose can be calculated by (Eq. 1) using the cancer slope factor reported by the U.S. Environmental Protection Agency (USEPA) and a one-in-a-million risk.

$$ADD = \frac{\text{Risk}}{CSF} \quad \text{(Eq. 1)}$$

Where

| | | |
|---|---|---|
| ADD | = | Allowable daily dose (mg/kg/day) |
| CSF | = | Cancer slope factor (mg/kg/day)$^{-1}$ |
| Risk | = | $10^{-6}$, which represents a one-in-a-million risk |

For non-carcinogens with chronic toxicity, the allowable daily dose is calculated by (Eq. 2) using the USEPA reference dose for chronic, non-cancer toxicity:

$$ADD = RfD \quad \text{(Eq. 2)}$$

Where

| | | |
|---|---|---|
| ADD | = | Allowable daily dose (mg/kg/day) |
| RfD | = | Reference dose (mg/kg/day) |

For chemicals for which the EPA has established maximum contaminant levels in drinking water, the allowable daily dose is calculated by (Eq. 3) as follows:

$$ADD = \frac{MCL \times W}{BW} \quad \text{(Eq. 3)}$$

Where

| | | |
|---|---|---|
| ADD | = | Allowable daily dose (mg/kg/day) |
| MCL | = | Maximum contaminate level (mg/Liter) |
| W | = | Volume of water consumed by an adult in a day = 2 Liter/day |
| BW | = | Body weight of an adult human = 70 kg |

As stated above, the allowable daily dose in these examples is an estimation of the dose resulting in a one-in-a-million risk of a toxicological effect.

The next part of the present invention converts this allowable daily dose (ADD) to an exposure based upon the use of the product. For example, for products to be used for food packaging the appropriate equation (Eq. 4) is as follows:

$$AC = \frac{ADD \times \frac{FC}{B} \times \frac{BW}{F \times CF}}{M} \quad \text{(Eq. 4)}$$

Where

| | | |
|---|---|---|
| AC | = | Allowable concentration (mg of chemical/kg of paperboard) |
| ADD | = | Allowable daily dose (mg/kg/day) |
| FC | = | Food-contact per surface area of packaging = 10 grams/inch$^{-2}$ |
| F | = | Total intake of food per day = 3 kilogram/day |
| CF | = | Fraction of food in contact with packaging (defined as the "consumption factor" by the FDA) |
| BW | = | Body weight of an adult human = 70 kg |
| M | = | Migration factor |

By choice of an appropriate consumption factor (CF) value, Equation (4) is applicable for polymer-coated paperboard (CF=0.21), uncoated paperboard (CF=0.1), glass (CF=0.08) or polymers (CF=0.41). Other modifications to this equation can include choosing a different value for body weight that reflects a targeted subgroup of the human population.

One also needs to assign a value for the migration factor. For food packaging, this factor reflects the percentage of chemical migrating from the package into the food. The most conservative assumption for food packaging would be to assume that all of the component chemical migrates from the packaging, which is M=1. This highly conservative approach is preferred unless specific and appropriate migration information is available.

As noted above, this example calculates the toxicological risk associated with the use of food packaging; however, other exposure scenarios can be calculated. For example, one can calculate the toxicological risk to a worker of a chemical migrating from paper being handled in the office.

Using the above values and choosing, for this example, food packaged in both polymer coated and uncoated paperboard (i.e., CF=0.1+0.21=0.31), Equation (4) can be simplified to Eq. 5:

$$AC = 4320/\text{day} \times ADD \text{ (mg/kg/day)} \quad \text{(Eq. 5)}$$

In Equation (5) the allowable daily dose based upon a one-in-a-million risk of toxicological effect can be converted into a concentration of a chemical in the paper packaging which has the same one-in-a-million risk.

Many manufacturers track their ingredient usage by calculating the weight of additive per weight of a final product. For example, this could be grams of additive per kilogram of polymer, pounds of additive per ton of pulp, etc. Thus, to make the present invention of more utility, the allowable concentration of a chemical component in paperboard (AC) should be converted to an "allowable addition rate", based upon the concentration of the chemical component in the additive. This can be expressed as follows in (Eq. 6):

$$AAR \text{ (mg additive/kg paperboard)} = \frac{AC \text{ (mg chemical/kg paperboard)}}{C_c \text{ (mg chemical/kg additive)}} \times C_v \text{ (mg/kg)} \quad \text{(Eq. 6)}$$

Where

| | | |
|---|---|---|
| AAR | = | Allowable addition rate of an additive in paperboard per kilogram of dry fiber |
| AC | = | Allowable concentration of chemical component per kilogram of dry fiber |
| $C_c$ | = | Concentration of chemical component in the additive |
| $C_v$ | = | Conversion factor = $10^6$ milligram/1 kilogram |

It is to be understood that Equation (6) is solely based upon the toxicity of the chemical component, the concentration of the component in the additive and conservative assumptions regarding the migration characteristics of the chemical component. This equation specifically does not include information about the actual addition rate of the additive used by the manufacturer.

The resulting value (AAR) in Equation (6) is no longer in terms of the individual chemical component, but rather it has been converted to a term based upon the additive. As previously mentioned, this is important because measurements in a manufacturing facility are, typically, based upon, and measured, using addition rates.

It is important to remember that a single additive will typically have multiple chemical components. Since these different chemical components will likely have different toxicity characteristics, by implication from equations presented above, an additive will have multiple allowable addition rates.

The calculated allowable addition rate for each chemical component in an additive from Equation (6) is compared to the actual addition rate used in the production facility. If the AAR (i.e., the toxicologically allowable addition rate) is greater than the actual addition rate used in production, then no further work needs to be performed. However, in the event that the actual addition rate used in production exceeds the allowable addition rate, then the additive and the specific chemical are clearly identified and marked (or flagged).

The specific flag used for a chemical component is dependent on the difference between the actual addition rate and the calculated allowable addition rate. If the difference is small, i.e., <10%, then the program responds by listing certain easily performed actions. As the difference between values increases, the complexity and the cost of the resolution increases.

The following TABLE illustrates examples of the relative differences and association actions. (Note: These examples are not intended to limit the scope of the invention.)

TABLE

| Difference in Toxicological and Actual Addition Rates | Action of Options |
|---|---|
| Less than 10% | Review values entered into the program and any assumptions |
| | Contact suppliers to ascertain if values provided reflect current product supplied to facility |
| | Have results reviewed by a qualified toxicological analyst |
| Less than 100% | Contact suppliers to ascertain if values provide reflect current product supplied to facility |
| | Have qualified professional review the physical properties of the specific chemical to identify if the compound is eliminated during processing, i.e., the volatilization of compounds with low boiling points. |
| | Have results reviewed by a qualified toxicological analyst |
| Greater than two orders of magnitude (>100%) | Consider performing specific migration analysis for the chemical in question |
| | Have results reviewed by a qualified toxicological analyst |

The flagging step is very important to the present invention because it acts as a filter for the data. This filtering eliminates all the non-essential information about the chemical components which allows the user to focus on those items that require further work. Furthermore, the present invention enables a person not suitably skilled to use the present invention; therefore, people skilled in the art (i.e., toxicologists, etc.) only have to investigate flagged chemical components and not all chemicals that make up an additive. This affords a significant cost savings. It is to be understood that the flow chart of the FIGURE, Equations 1–6 and the TABLE can be conventionally placed in a suitable computer so that they can be more easily utilized when attempting to employ the novel aspects of the present invention.

It is to be understood that the utility of the present invention is not limited to determining product safety. It can also be modified for use in identifying potential environmental and safety problems. For example, one could assume that all materials with a boiling point less than a certain temperature will be volatilized during the manufacturing process. Therefore, one could calculate if the amount of these chemicals exceeds various safety and environmental limits.

Once given the above disclosure, many other features, modifications or improvements will become apparent to the skilled artisan. Such features, modifications or improvements are, therefore, considered to be a part of this invention, the scope of which is to be determined by the following claims.

What is claimed is:

1. A method for determining if a chemical additive used in the manufacture of paper packaging will contain a chemical component or reaction product that is of toxicological concern to a consumer of said paper packaging as a result of the addition of said chemical additive to a manufacturing process to manufacture paper packaging, wherein said method comprises the steps of:

(1) cataloging a plurality of chemical additives which will be added to a paper packaging manufacturing process and amounts of said chemical additives which are originally desired to be added;

(2) determining an actual concentration of said chemical component and reaction product in said chemical additives which will be added to said paper packaging manufacturing process;

(3) calculating a toxicologically allowable concentration of said chemical component and said reaction product in said paper packaging which will be produced by said paper packaging manufacturing process;

(4) comparing said toxicologically allowable concentration with said actual concentration;

(5) identifying, if any, chemical component and reaction product and their actual concentrations which are greater than said toxicologically allowable concentration; and (6) adjusting, if necessary, said actual concentration such that said actual concentration is no greater than said allowable concentration, wherein for differences between said allowable and said actual concentration which are less than 10% of the allowable concentration, said method further comprises the step of:

(7) contacting any supplier of said chemical additive which will be added to said paper packaging manufacturing process which will produce said chemical component or reaction product that will have an actual concentration greater than said allowable concentration, (8) recalculating said actual concentration of said chemical component or reaction product that have an actual concentration greater than said toxicologically allowable concentration, and (9) employing a qualified toxicological analyst to review said actual concentration, said allowable concentration, and said comparison between said actual and allowable concentrations, to determine if such a difference between said actual and allowable concentrations warrants a toxicological concern to a consumer of said paper packaging.

2. The method, as in claim 1, wherein for differences between said toxicologically allowable and said actual concentrations which are between 10% and 100% of said allowable concentration, said method further comprises the step of:

determining if said chemical component or reaction product which have allowable versus actual concentration differences of between 10% and 100% of said allowable concentration will be eliminated during said manufacturing process.

3. The method, as in claim 2, wherein for differences between said toxicologically allowable and said actual concentrations which are greater than 100% of said allowable concentration, said method further comprises the step of:

performing a migration analysis of said chemical component and reaction product which have allowable versus actual concentrations greater than 100% of said allowable concentration.

* * * * *